United States Patent [19]

Turin et al.

[11] 4,016,154
[45] Apr. 5, 1977

[54] NOVEL DERIVATIVE OF N-(3,4,5-TRIMETHOXY CINNAMOYL) PIPERAZINE, ITS ACID ADDITION SALTS, ITS PROCESS OF PREPARATION AND ITS THERAPEUTIC APPLICATION

[75] Inventors: Michel J. Turin, Paris; Guy M. Raynaud, Meudon La Foret; Bernard M. Pourrias, Rueil Malmaison; Patrick G. Guerret, Paris, all of France

[73] Assignee: Delalande S.A., Courbevoie, France

[22] Filed: July 15, 1975

[21] Appl. No.: 596,041

[30] Foreign Application Priority Data

July 17, 1974 France .................. 74.24831

[52] U.S. Cl. .......... 260/240 J; 260/268 C; 424/250
[51] Int. Cl.$^2$ ...................... C07D 403/02
[58] Field of Search ........... 260/240 J, 268 C; 424/250

[56] References Cited

UNITED STATES PATENTS

| | | | |
|---|---|---|---|
| 3,634,411 | 1/1972 | Fauran et al. | 424/250 |
| 3,798,325 | 3/1974 | Schindler et al. | 424/250 |
| 3,806,510 | 4/1974 | Parcell | 424/250 |
| 3,826,833 | 7/1974 | Schindler et al. | 424/250 |
| 3,828,046 | 8/1974 | Doerhoefer | 424/250 |
| 3,856,958 | 12/1974 | Lee | 424/250 |

OTHER PUBLICATIONS

Turbanti et al., Chimica Therapeutica, vol. II (1967), p. 354.

*Primary Examiner* — Arthur P. Demers
*Attorney, Agent, or Firm* — Woodhams, Blanchard and Flynn

[57] ABSTRACT

A compound having the formula

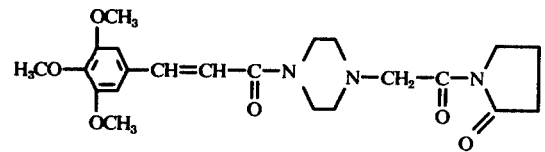

and its pharmacologically acceptable acid addition salts. The compound is prepared by condensing N-(3,4,5-trimethoxy cinnamoyl) piperazine with N-(2-pyrrolidinone) chloroacetamide. The compounds possess peripheral and coronary vasodilatatory properties and hypotensive and antihypertensive properties.

2 Claims, No Drawings

NOVEL DERIVATIVE OF N-(3,4,5-TRIMETHOXY CINNAMOYL) PIPERAZINE, ITS ACID ADDITION SALTS, ITS PROCESS OF PREPARATION AND ITS THERAPEUTIC APPLICATION

The present invention relates to a novel derivative of N-(3,4,5-trimethoxy cinnamoyl) piperazine, its acid addition salts, its process of preparation and its therapeutic application.

The derivative according to the invention is N-(3,4,5-trimethoxy cinnamoyl)-N'-(2'-pyrrolidinone-1'-carbonylmethyl)piperazine, of formula (I):

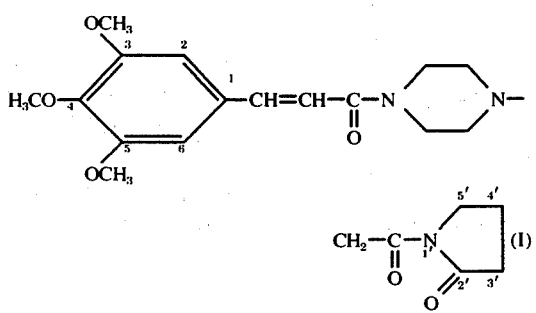

The preferred addition salt is the maleate.

The process according to the invention consists in condensing N-(3,4,5-trimethoxy cinnamoyl) piperazine of formula (II):

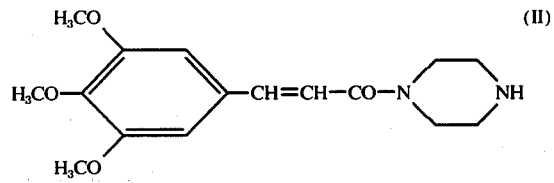

with N-(2-pyrrolidinone)chloracetamide of formula (III):

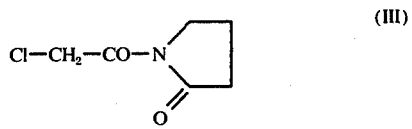

in an ethyl acetate medium, under reflux, and in the presence of sodium carbonate.

The compound of formula (III) is itself prepared by condensing a mole of chloroacetyl chloride of formula (IV):

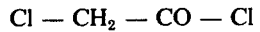

with a mole of 2-pyrrolidinone of formula (V):

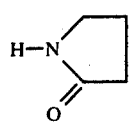

A convenient mode of operation for the synthesis of the compound of formula (I) is given in the following example.

EXAMPLE:

N-(3,4,5-trimethoxy cinnamoyl)-N'-(2'-pyrrolidinone-1'-carbonylmethyl)piperazine
Code No. 740194

1st stage : N-(2-pyrrolidinone)chloracetamide.
Code No. 740193

Two moles of 2-pyrrolidinone is added to a benzenic solution of a mole of chloracetyl chloride. After remaining in contact for 24 hours at ambient temperature, the benzenic solution is concentrated.

The crude product obtained is purified by distillation.
Boiling point under 0.001 mm Hg = 112° C
Yield = 73%

2nd stage : N-(3,4,5-trimethoxy cinnamoyl)-N'-(2'-pyrrolidinone-1'-carbonylmethyl)piperazine.
Code No. 740194

0.12 mole of sodium carbonate and 0.057 mole of N-(2-pyrrolidinone)chloracetamide obtained from the preceding stage, and carrying the Code No. 740193, are added to a solution under reflux of 0.057 mole of N-(3,4,5-trimethoxy cinnamoyl)piperazine, in 100 ml of ethyl acetate.

After refluxing for three hours, the reaction medium is concentrated, the evaporation residue is taken up in water and in chloroform, decanted, dried and the organic phase is concentrated.

The crude product obtained is purified by recrystallisation from absolute ethanol. The compound of Code No. 740194 crystallizes with one molecule of water.
Yield = 32%
Melting point = 100° C
Empirical formula = $C_{22}H_{29}N_3O_6$, $H_2O$
Elementary analysis:

|  | C | H | N |
|---|---|---|---|
| Calculated (%) | 58.78 | 6.95 | 9.35 |
| Found (%) | 59.00 | 6.92 | 9.23 |

The base thus obtained is salified in an acetonic medium with the aid of maleic acid.
Yield = 80%
Melting point = 174° C
Empirical formula = $C_{26}H_{33}N_3O_{10}$
Elementary analysis:

|  | C | H | N |
|---|---|---|---|
| Calculated (%) | 57.03 | 6.03 | 7.68 |
| Found (%) | 56.94 | 6.04 | 7.69 |

The compound of formula (I) corresponds to the major urinary metabolite in man and dog of N-(3,4,5-trimethoxy cinnamoyl)-N'-(pyrrolidino carbonyl methyl)piperazine, a compound utilised in human therapeutics as a vasodilatatory agent.

This metabolite, studied on animals in the laboratory, has shown a notable activity in the cardiovascular domain.

More precisely, the compound of formula (I) has been shown to possess peripheral and coronary vasodilatatory properties as well as hypotensive and antihypertensive properties.

1. Peripheral vasodilatatory action.

The compound of formula (I), administered by intra-arterial means in a dose which will not affect the arterial pressure, provokes an augmentation of flow of the femoral artery, in which the injection is made, in an anaesthetised dog with femoral carotid anastomosis, the measurement being effected by means of an electromagnetic flowmeter situated at the level of the derivation.

Thus, the femoral flow is augmented by 70% for 2 minutes following the administration of 500 μg/Kg/i.a. of the compound of formula (I).

2. Coronary vasodilatory action.

Administered by intraveinous means to the anaesthetised dog, the compound of formula (I) provokes an augmentation of flow of the anterior interventricular artery, the measurement being effected by means of an electromagnetic flowmeter placed on this artery.

By way of example, said flow is augmented by 165% for 22 minutes following the administration of 10mg/Kg/i.v. of the compound of formula (I).

3. Hypotensive action.

Administered by intraveinous means to an anaesthetised cat, the compound of formula (I) lowers the systolic arterial pressure and the diastolic arterial pressure.

Thus, by administration of 12.5 mg/Kg/i.v. of the compound of formula (I), there is observed, for 1½ to 2 hours, a diminution of 20% in the systolic arterial pressure, and of 35% in the diastolic arterial pressure.

4. Antihypertensive action.

The compound of formula (I), administered by oral means to a rat genetically suffering from high blood pressure, is capable of lowering the systolic arterial pressure.

By way of example, said pressure is lowered by 20% by a dose of 100 mg/Kg/p.o.

As well, the compound of formula (I) is little toxic, since its lethal dose (LD50) by intraveinous means in the mouse is (510 ± 15) mg/Kg.

The compound of formula (I) is useful in the treatment of peripheral and coronary circulatory insufficiencies and hypertension.

It is administered by oral means in the form of tablets, gelules or dragees containing 50 to 400 mg/Kg of active ingredient (1 to 5 per day), in the form of drinkable drops containing 0.5 to 5.0% of active ingredient (20 to 50 drops - 1 to 3 times a day), by parenteral means in the form of injectable ampoules containing 10 to 200 mg of active ingredient (1 to 3 per day) and by rectal means in the form of suppositories containing 20 to 150 mg of active ingredient (1 to 3 per day).

Accordingly, the invention also provides a therapeutic composition comprising the compound of formula (I), or an acid-addition salt thereof, together with a therapeutically-acceptable carrier.

What we claim is:

1. N-(3,4,5-trimethoxy cinnamoyl)-N'-(2'-pyrrolidinone-1'-carbonylmethyl) piperazine of formula (I):

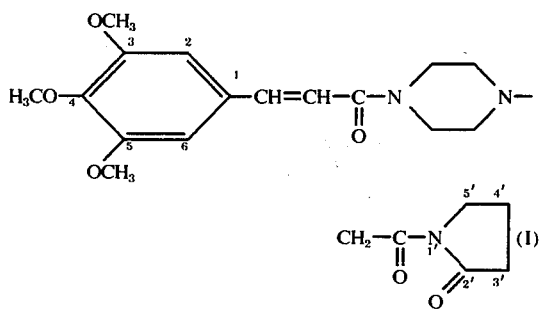

and the pharmacologically acceptable acid addition salts thereof.

2. The maleate of N-(3,4,5-trimethoxy cinnamoyl)-N'-(2'-pyrrolidinone-1'-carbonylmethyl) piperazine.

* * * * *